United States Patent [19]

Covino-Hrbacek et al.

[11] Patent Number: 5,103,678
[45] Date of Patent: Apr. 14, 1992

[54] FIBER PEEL FORCE MEASURING APPARATUS

[75] Inventors: Josephine Covino-Hrbacek; Albert H. Lepie; Thomas S. Stephens, all of Ridgecrest, Calif.

[73] Assignee: The United States of America as represented by the Secretary of the Navy, Washington, D.C.

[21] Appl. No.: 697,351

[22] Filed: May 6, 1991

[51] Int. Cl.⁵ .............................................. G01N 3/08
[52] U.S. Cl. .................................. 73/828; 74/862.39
[58] Field of Search ................... 73/828, 862.44, 865.3, 73/862.39, 862.42, 841; 242/128

[56] References Cited

U.S. PATENT DOCUMENTS 2,037,273 4/1936 Scott ................................. 73/828 X Primary Examiner—Jerry W. Myracle
Attorney, Agent, or Firm—Harvey A. Gilbert; Melvin J. Sliwka; John L. Forrest, Jr.

[57] ABSTRACT

Apparatus for measuring peel force exerted on optical fiber being pulled from a bobbin upon which it is wound, the pull being in the direction of the longitudinal axis of the truncated-conically-shaped bobbin. One end of an elongaged lever arm holds the bobbin cantilevered from the bobbin end opposite that from which the optical fiber is pulled so that the bobbin is positioned generally horizontally over a horizontal base to which the opposite end of the lever arm is pivotally attached. An intermediate point on the arm beneath the bobbin is in contact with a load measuring device so that as the fiber is pulled any reaction by the arm upon the device provides a measure of the peel force upon the fiber.

5 Claims, 2 Drawing Sheets

FIBER PEEL FORCE MEASURING APPARATUS

BACKGROUND OF THE INVENTION

The present invention relates to optical fiber peel force measurements and in particular to an apparatus for measuring peel force required to remove optical fiber from a bobbin upon which it is wound.

The use of optical fiber in airborne communication, guidance, and control systems is increasing as is demand for covert signal communication without the introduction of multi-causal interference. Handling of optical fiber even under controlled laboratory conditions is difficult at best, particularly in relation to the generally fragile nature of the fiber. Removing the fiber from a bobbin upon which it is wound increases the risks for fiber damage considerably. When the fiber is being pulled from its wound condition on one or two bobbins during in-flight maneuvers, the risk of catastrophic damage to the fiber and interruption of signals carried by the fiber becomes very substantial. Devices and methods for measuring the peel force being applied to a fiber wound upon a bobbin as it is pulled during its removal from the bobbin and dispensed to the aircraft operations environment exist in a variety of configurations and complexities.

SUMMARY OF THE INVENTION

It is thus an object of the present invention to provide a means for measuring the peel force applied to optical fiber when removing it from its wound condition upon a bobbin by application of a force to the fiber parallel to and in the direction of the longitudinal axis of the bobbin. It is another object of the present invention to provide a sensitive means for leveraging the actual peel force applied to remove optical fiber from its wound condition upon a bobbin to permit accurate measurement of peel force magnitude.

The present invention is an apparatus employing a lever arm pivotally attached to rotate in a vertical plane about the horizontal base to which it is attached. A nearby vertical support member, one-quarter to one-third the length of the lever arm is attached to one end of the base. The opposite end of the short support member holds a load cell or other load measuring means which is directed horizontally in the direction of and in juxtaposition with the lever arm. The end of the lever arm opposite its pivotal connection to the base is attached to one end of the bobbin upon which optical fiber has been wound so that the bobbin extends cantilevered over the base from the end of the lever arm. Until the fiber is pulled from the bobbin, the lever arm rests against a vibration damping pad sandwiched between the arm and the load cell which extends horizontally from the vertical support member to which it is attached. As the fiber is peeled from the bobbin, the lever arm is caused to rotate against the load cell which then produces an output proportional to the peel force removing the optical fiber from the bobbin.

A digital oscilloscope or similar display or readout device may be used to read peel force output signal from the load cell during tests.

These and other objects, advantages and features will be more clearly understood when the detailed description of the present invention, which follows, is read in light of the accompanying drawings.

DRAWINGS

In the drawings: FIG. 1 is a perspective view of the invention. FIG. 2 is a side view of the invention.

DETAILED DESCRIPTION

Figure 1:
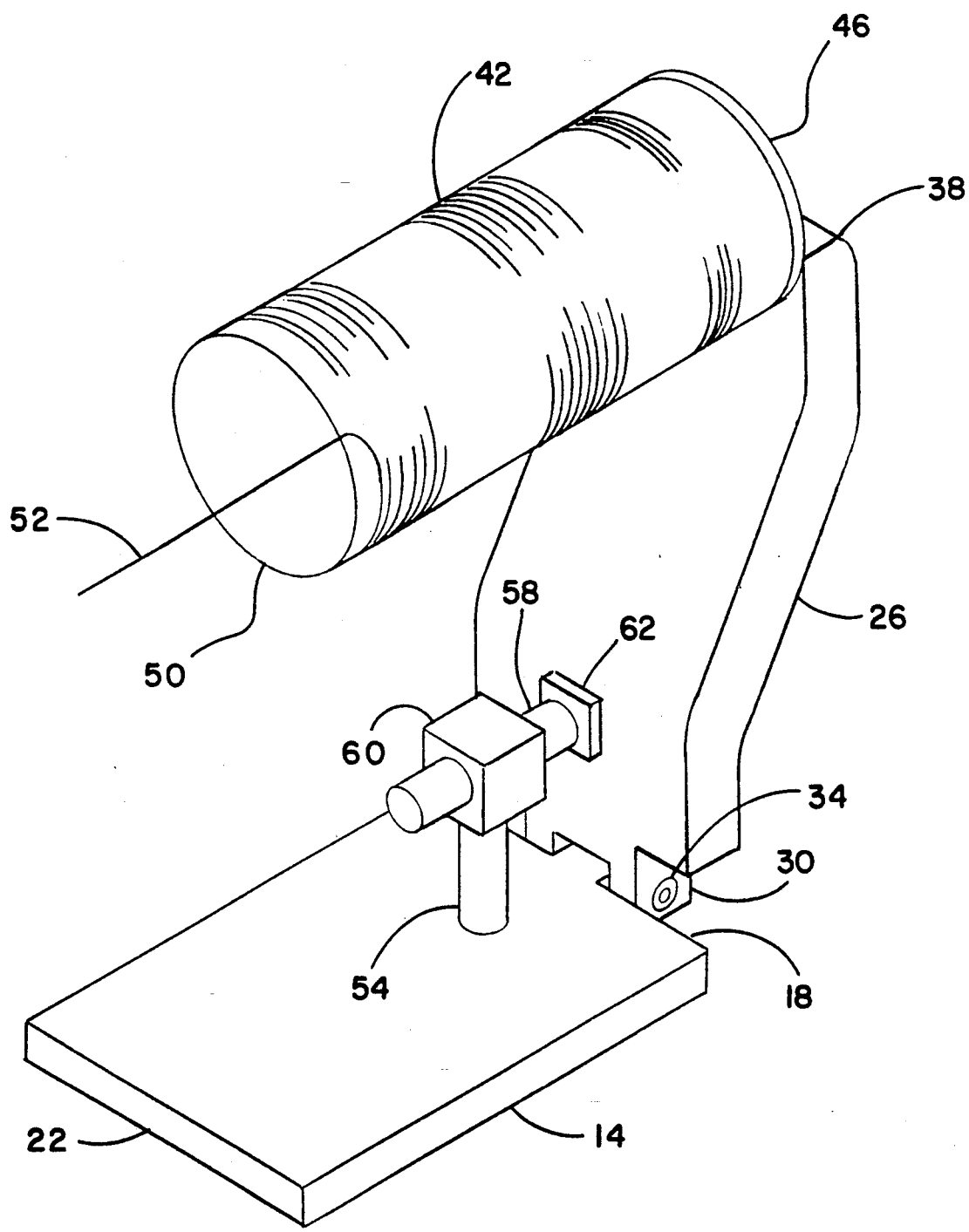
Figure 2:
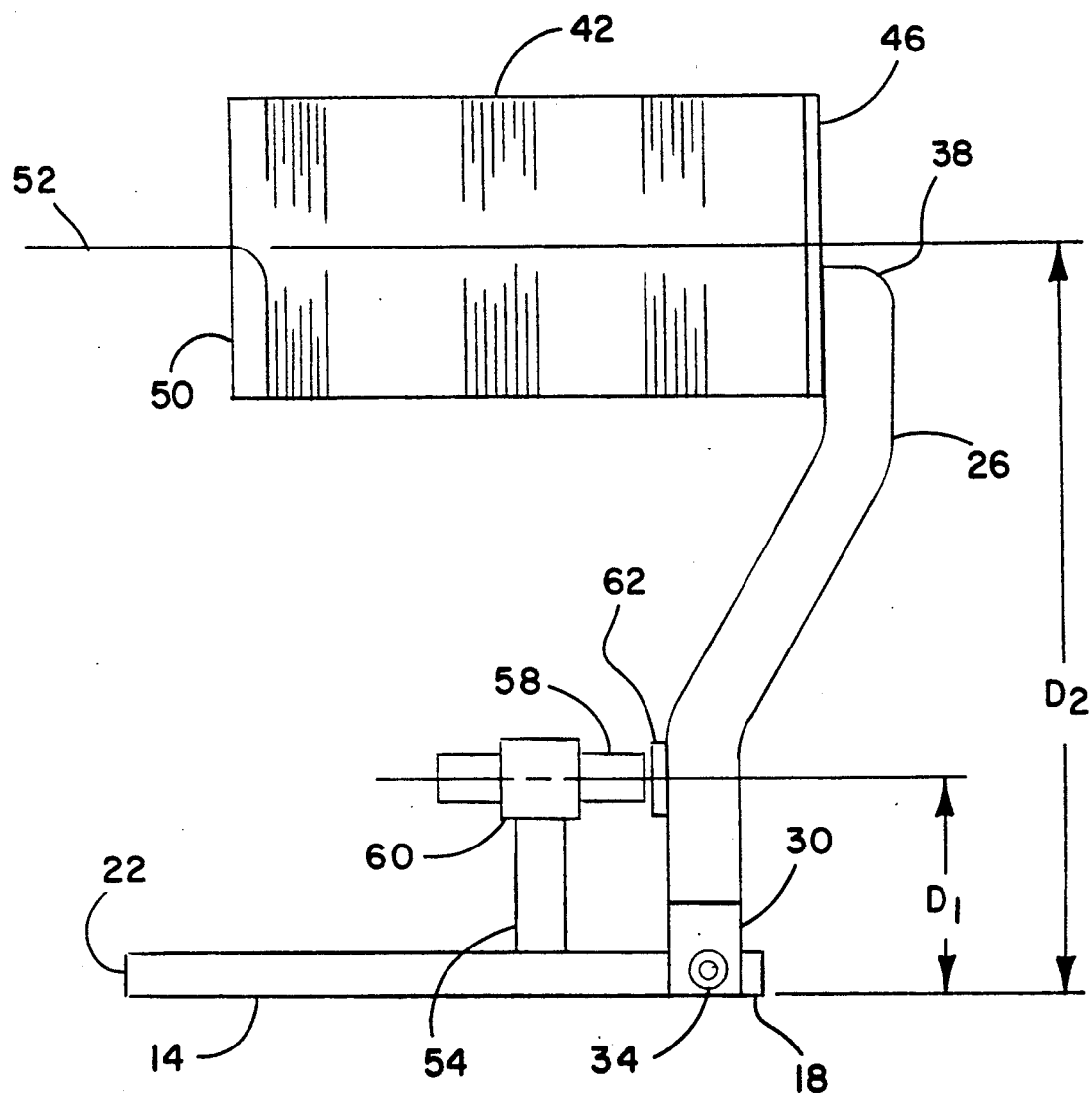

Referring to FIGS. 1 and 2 of the present invention, the peel force measuring apparatus 10 is shown. The peel force measuring apparatus 10 comprises the base 14 having a first end 18 and an opposite second end 22. The first support member 26 extends from its pivotally connected end 30 secured by a low friction bearing 34 to the first end 18 of the base 14. In lieu of the direct pivotal connection of the first support member 26 with the base 14, a low friction hinge may be used to provide the connection. The free end 38 of the first support member 26 is the location at which the bobbin 42 is attached at its end 46. The bobbin 42 is shown as typically configured in the shape of a truncated cone with the free end 50 of slightly lesser diameter than the end 46 of the bobbin attached to the first support member 26. The optical fiber 52 is shown in the figures being pulled from the free end 50 of the bobbin 42 upon which it is initially wound.

The second support member 54 extends vertically from the base 14 in juxtaposition with the first support member 26. The load cell 58 is affixed to the upper end 60 of the second support member 54 and extends horizontally and in parallel with the base 14 into contact with the vibration damping pad 62 which is affixed within the area of contact on the first support member 26 with the load cell 58.

It should be noted that the load cell 58 is horizontally adjustable so that a no-load output from the load-cell 58 can be set as desired when the bobbin 42 is mounted for test but no pull force is applied to the optical fiber 52. Not shown in the figures is the electrical connection from the load cell 58 to a readout or display device such as a digital oscilloscope.

The peel force, or tension in the fiber, is equal to the force on the load cell 58 multiplied by the mechanical advantage. The mechanical advantage is the ratio of the perpendicular distance $D_2$ from the hinge to a line through the fiber 52, to the distance from the hinge to the point of contact between the load cell and the lever $D_1$. Thus, $D_2/D_1$ is the ratio and the distances $D_1$ and $D_2$ are as shown in FIG. 2.

The load cell 58 used in the preferred embodiment has an accuracy of 0.1 g. Peel forces can be measured as a function of "pay-out" speeds and measurements from 0.0278 ft/sec to 700+ ft/sec using the present invention can be obtained. The vibration damping pad 62 is fabricated from leather or rubberized fabric to attenuate high frequency oscillations in the force signal produced by the load cell 58.

OPERATION

With reference to FIGS. 1 and 2 the end 46 of a bobbin 42 pre-wound with optical fiber is affixed to the free end 38 of the first support member 26. Attachment is accomplished by bolting, however, other means are possible depending on the bobbin configuration under test.

Once the bobbin 42 is secured to the first support member 26 the weight of the bobbin will cause the member 26 to react through the attached vibration damping pad upon the load cell 58. The load cell is then adjusted in the horizontal direction so that the load it senses before fiber peel commences is zero or some minimum value. At that point testing can begin by applying a pull force to the fiber 52 to cause it to be removed from the free end 50 of the bobbin 42.

Various changes may be made in the form, construction, and arrangement of parts of the present invention without departing from its spirit, scope, and advantages. The embodiment described herein is merely exemplary and the invention is intended to be fully encompassed by the claims which follow.

What we now claim for our invention is:

1. An apparatus for measuring peel force applied to optical fiber being removably pulled from one end of a bobbin about which it is wound, said apparatus comprising:

a base having a first end and an opposite second end;

a first elongated and rigid support member vertically extending from and having one end pivotally connected to the first end of said base, said first support member having a free end opposite said pivotally connected end, said free end adapted to be removably affixed to the end of said bobbin opposite the end from which said optical fiber is removed cantilevered over said base in the direction of said second end;

a second elongated and rigid support member vertically extending from and having one end affixed to said base in juxtaposition and in parallel with said first support, between said first support and the second end of said base, said second support measuring between one-third and one-half the length of said first support;

a means attached to the end of said second support member opposite said base and extending to a spaced distance from said first support member for measuring the force directed thereupon; and a means affixed to said first support member, extending towards said measuring means and occupying the space there-between, for damping vibrations when said first member is caused to move arcuately about its pivot and against said load measuring means.

2. The apparatus of claim 1 wherein said means for measuring forces is adjustably and removably attached to the end of said second support member.

3. The apparatus of claim 1 wherein said means for damping vibrations is leather.

4. The apparatus of claim 1 wherein said means for damping vibrations is rubberized fabric.

5. The apparatus of claim 1 wherein said means of measuring the force loads is a load cell.

* * * * *